United States Patent [19]

Lempert et al.

[11] 4,434,099
[45] Feb. 28, 1984

[54] BETA-LACTAM COMPOUNDS CONTAINING A PROTECTED C-ACETYL GROUP, PROCESS FOR THEIR PREPARATION AND PHARMACEUTICAL COMPOSITIONS CONTAINING THEM

[75] Inventors: Karoly Lempert; Kalman Harsanyi; Gabor Doleschall; Gyula Hornyak; Jozsef Nyitrai, all of Budapest; Karoly Zauer, Szentendre; Jozsef Fetter, Budapest; Gyula Simig, Budapest; Zsuzsanna Gombos nee Visky, Budapest; Gizella Szalai nee Barta, Vecses, all of Hungary

[73] Assignee: Richter Gedeon Vegyeszeti Gyar Rt., Budapest, Hungary

[21] Appl. No.: 301,883

[22] Filed: Sep. 11, 1981

[30] Foreign Application Priority Data

Sep. 15, 1980 [HU] Hungary .............................. 2263/80

[51] Int. Cl.³ .................. C07D 205/08; C07D 407/04
[52] U.S. Cl. .......................... 260/239 A; 260/330.9;
 260/245.2 T; 562/568; 548/533
[58] Field of Search .......................... 260/330.9, 239 A

[56] References Cited

U.S. PATENT DOCUMENTS 4,290,947 9/1981 Christensen .................... 260/239 A
4,322,345 3/1982 Hirata et al. .................... 260/239 A Primary Examiner—Mark L. Berch
Attorney, Agent, or Firm—Karl F. Ross; Herbert Dubno

[57] ABSTRACT

The invention relates to new heterocyclic compounds containing a protected C-acetyl group. More particulary, the invention concerns new compounds of the formula (VI)

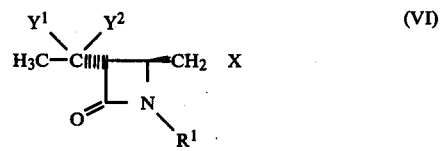

wherein
$R^1$ is hydrogen or a group suitable for a temporary protection or amides,
X is hydroxyl, halogen, cyano or an $-O-SO_2-R^2$ group, in which
$R^2$ is lower alkyl or aryl,
$Y^1$ and $Y^2$ together form a group suitable for a temporary protection of a keto group.

The new compounds possess anaphylactic properties and are valuable intermediates of thienamycin synthesis. Their preparation and the new intermediates obtained during their preparation are also within the scope of the invention.

8 Claims, No Drawings

BETA-LACTAM COMPOUNDS CONTAINING A PROTECTED C-ACETYL GROUP, PROCESS FOR THEIR PREPARATION AND PHARMACEUTICAL COMPOSITIONS CONTAINING THEM

The invention relates to heterocyclic compounds containing a protected C-acetyl group.

According to an aspect of the invention there are provided new compounds of the formula (VI)

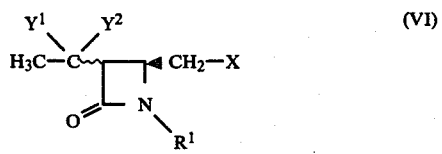

wherein
$R^1$ is hydrogen or a group suitable for temporary protection of amides;
X is hydroxyl, halogen, cyano or an $-O-SO_2-R^2$ group, in which $R^2$ is lower alkyl or aryl, and
$Y^1$ and $Y^2$ together form a group suitable for temporary protection of a keto group.

In the definition of $R^1$ the term "a group suitable for temporary protection of amides" preferably refers to benzyl which can be substituted with one or more methoxy groups.

The term "lower alkyl" in the definition of $R^2$ preferably stands for methyl while a preferred aryl group is tolyl.

The preferred representatives of the groups suitable for a temporary protection of a keto group in the definition of $Y^1$ and $Y^2$ are ketals and thio-analogs thereof.

The compounds of the formula (VI) show antihypoxic activity and, together with the new compounds of the formula (V)

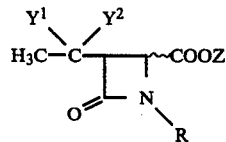

wherein
$Y^1$ and $Y^2$ are as hereinabove defined,
Z is alkyl, and
R is a group suitable for a temporary protection of amides, are valuable intermediates of a new synthesis route to thienamycin. The new compounds of the formula (V) form another aspect of the invention.

In the definition of Z the term "alkyl" preferably is used to refer to lower alkyls, more preferably methyl or ethyl. The new intermediates of the formulae (VI) and (V) can be prepared more conveniently and with a higher yield than the hitherto known intermediates of thienamycin synthesis. Starting from these compounds, thienamycin can be prepared for example as illustrated on the Chart annexed hereto as the last page of the specification.

In the most preferred compounds of the formula (VI), $R^1$ stands for dimethoxybenzyl, $Y^1$, $Y^2$ and X are as defined hereinbefore.

Thienamycin is a well known antibiotic with a wide spectrum of activity, which has first been prepared by a microbiological method disclosed in the U.S. patent specification No. 3,950,357 and later by a chemical synthesis which was reported in the published German patent application No. 2,751,597.

Our intention was to provide a new synthesis route for the preparation of thienamycin, in which the azetidinone-skeleton and the α-hydroxyethyl side-chain (or a side-chain, which can be easily converted into this group) are formed simultaneously at the beginning and the key intermediate obtained in this way is then converted into thienamycin.

We have found that by acylating a dialkyl (substituted amino)-malonate of the formula (I)

$$R-NH-CH(COOZ)_2 \qquad (I)$$

wherein
R is a group suitable for a temporary protection of amides, preferably benzyl which can be substituted with one or more methoxy groups,
Z is alkyl, preferably methyl or ethyl, with diketene and reacting the compound of the formula (IIa)

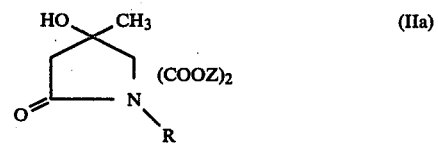

which can be accompanied by a compound of the formula (IIb)

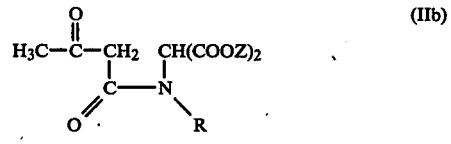

with an alkali metal alcoholate and iodine or a similar reactant, an azetidionone of the formula (III)

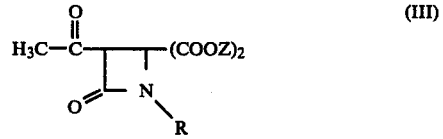

which contains an α-acetyl side-chain is obtained. This compound is a suitable key intermediate. The further compounds of the formula (III) can be prepared in an analogous way.

The present invention relates to the conversion of the compounds of the formula (III), into compound of the formula (V) and optionally into compound of the formula (VI), which possess valuable antibacterial activity and are valuable intermediates in the synthesis of thienamycin.

According to our experiments it is desirable to protect the keto group in the α-C-acetyl side-chain of a compound of the formula (III) by a suitable protecting group prior to conversion into thienamycin. The protecting group serves for a temporary protection only, and should later be eliminated. Preferred protecting groups are the ketal groups and thioanalogs thereof. The ethyleneketal or hemithioketal protecting group is preferably formed by means of ethylene glycol or a thioanalog thereof, for example mercapto-ethanol, and the compound of the formula (IV)

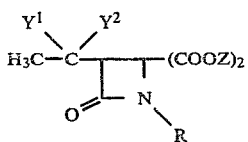

obtained is reacted with an alkali metal halide in pyridine or a similar solvent or in aqueous dimethyl sulfoxide to give a corresponding compound of the formula (V).

The compound of the formula (V) is a mixture of cis and trans isomers and if desired, can be converted into thienamycin. If a compound of the formula (V) is reduced with an appropriately chosen complex metal hydride, preferably alkali metal tetrahydridoborate, a corresponding trans compound of the formula (VI) in which $R^1$ represents a group suitable for temporary protection of amides and X is hydroxyl, is obtained with a good yield. The compounds of the formula (VI) obtained in this way may be used as intermediates of thienamycin synthesis or may be converted into further intermediates of the formula (VI).

If a compound of the formula (VI) obtained by the above process (X being hydroxyl) is reacted with a lower alkane- or arenesulfonic acid halide, a compound of the formula (VI), in which X represents an $-O-SO_2-R^2$ group and $R^2$ is lower alkyl or aryl, is obtained.

Further compounds of the formula (VI), in which X represents a halogen atom, can be obtained by reacting a compound of the formula (VI), in which X stands for an $-O-SO_2-R^2$ group, with an alkali metal halide.

The compounds of the formula (VI), in which X is halogen may further be converted into corresponding compounds of the formula (VI), in which X stands for cyano by reacting with an alkali metal cyanide.

All these compounds are suitable for the preparation of thienamycin.

From the compounds of the formula (VI), in which X is an $-O-SO_2-R^2$ group and $R^1$ is dimethoxybenzyl, the group suitable for a temporary protection of amides can be split off by compounds of peroxidisulfate type, to yield compounds of the formula (VI) in which $R^1$ is hydrogen.

Compounds of the formula (IV), (V) and (VI) are new and may be used for the synthesis of thienamycin.

According to a further aspect of the invention there is provided a process for the preparation of compounds of the formula (VI) which comprises reacting a compound of the formula (III), wherein R and Z are as defined hereinbefore, with a compound suitable for a temporary protection of a keto group, preferably by a ketal forming agent or a thioanalog thereof, in the presence of a reaction-promoting agent, and further reacting a compound of the formula (IV) obtained with an alkali metal halide, in pyridine or a similar solvent or in aqueous dimethyl sulfoxide, and isolating the mixture of cis and trans compounds of the formula (V) obtained; or if desired, reacting it with a complex metal hydride, preferably alkali metal tetrahydroborate and isolating the resulting compound of the formula (VI), in which $R^1$ represents a group suitable for a temporary protection of amides and X stands for hydroxyl, or if desired, reacting it with a lower alkane- or arenesulfonic acid halide to give a compound of the formula (VI), in which X stands for an $-O-SO_2-R^2$ group, in which $R^2$ is lower alkyl, preferably methyl or aryl, preferably tolyl, and $R^1$ is a group suitable for a temporary protection of amides.

If desired, the compounds of the formula (VI) obtained by the above reactions may be subjected to additional conversions. More particularly, (a) a compound of the formula (VI) in which
X represents an $-O-SO_2R^2$ group, in which
$R^2$ stands for lower alkyl, preferably methyl, or for aryl, preferably tolyl, and
$R^1$ is a group suitable for a temporary protection of amides, can be isolated from the reaction mixture or, if desired, may be reacted with an alkali metal halide or a salt of an organic base with a hydrogen halide, and the compound of the formula (VI) obtained in which
X stands for halogen and
$R^1$ is a protecting group suitable for a temporary protection of amides, may be isolated or, if desired, reacted with an alkali metal cyanide and the compound of the formula (VI), in which
X is cyano and
$R^1$ is a protecting group suitable for temporary protection of amides,
obtained is isolated; or (b) a compound of the formula (VI) in which
X stands for an $-O-SO_2-R^2$ group, wherein $R^2$ has the same meaning as defined hereinbefore,
$R^1$ is dimethoxybenzyl, can be reacted with a compound of the peroxidisulfate type, preferably potassium or sodium peroxidisulfate, and the compound of the formula (VI) obtained may be converted into a corresponding compound of the formula (VI) in which X stands for halogen and $R^1$ is hydrogen, as described in process variant (a).

As a first step of the process according to the invention compounds of the formula (III) are converted into compounds of the formula (IV). As a reactant compound suitable for a temporary protection of keto groups, preferably ketal forming compounds or thioanalogs thereof, more preferably ethylene glycol or a thioanalog thereof are used. The reaction may be positively influenced by an appropriately chosen reaction promoter, such as borotrifluoride diethyletherate or an arenesulfonic acid, e.g. p-toluenesulfonic acid, naphthalenesulfonic acid, etc.

The reaction is carried out in the presence of an organic solvent, preferably benzene, toluene, dioxane, tetrahydrofuran, etc. The reaction temperature is between room temperature and the boiling temperature of the reaction mixture.

According to the second step of the synthesis a compound of the formula (IV) is reacted with an alkali metal halide, preferably sodium or lithium chloride, in the presence of pyridine, quinoline, the homologs or mixtures thereof, or preferably of a mixture of dimethyl sulfoxide and water to give a corresponding compound of the formula (V).

If desired, a compound of the formula (V), which is a mixture of cis and trans isomers is reduced in a third step of the process according to the invention and the trans compound of the formula (VI) obtained, in which $R^1$ is a protecting group suitable for a temporary protection of amides, $Y^1$ and $Y^2$ together are capable of temporary protection of a keto group, and X stands for hydroxyl is isolated. As a reducing agent a suitable complex metal hydride, preferably an alkali metal tetrahydroborate is used. As a solvent for example lower alkanols, preferably methanol or aqueous tetrahydrofurance can be employed.

If desired, a compound of the formula (VI) in which X is hydroxyl is converted into other compounds of the formula (VI). All the compounds obtained in this way have a trans configuration.

If a compound of the formula (VI), in which X is hydroxyl, $R^1$ represents a group suitable for a temporary protection of amides and $Y^1$ and $Y^2$ together form a group suitable for a temporary protection of a keto group is acted with an alkali metal halide, preferably sodium iodide or a salt of an organic base iwth a hydrogen halide, preferably iwth triethylamine hydrochloride or pyridinium hydrochloride, compounds of the formula (VI), in which X stands for halogen, $R^1$, $Y^1$ and $Y^2$ are as defined above, are obtained. This reaction may be carried out in usual solvents, preferably acetone.

If a compound of the formula (VI), in which X is halogen, $R^1$ is a group suitable for a temporary protection of amides and $Y^1$ and $Y^2$ together stand for a group suitable for a temporary protection of a keto group, is reacted with an alkali metal cyanide, a corresponding compound of the formula (VI) in which X stands for cyano is obtained. The reaction is preferably performed in a dipolar aprotic solvent, preferably dimethyl formamide, at room temperature.

From the compounds of the formula (VI), in which $R^1$ is dimethoxybenzyl, $Y^1$ and $Y^2$ are as defined above and X stands for an $—O—SO_2—R^2$ group, the dimethoxybenzyl protecting group can be eliminated in an oxidative way, preferably with a peroxidesulfate-type compound, preferably with potassium or sodium peroxidisulfate ($Na_2S_2O_8, K_2S_2O_8$).

The reaction is accomplished in the presence of a buffer of pH=7, water and an organic solvent.

Further details of the invention are illustrated by the following, nonlimiting Examples.

EXAMPLE 1

Diethyl-1-(2,4-dimethoxybenzyl)-3-(2-methyl-1,3-dioxolane-2-yl)-4-oxo-2,2-azetidine-dicarboxylate (compound of the formula (IV), in which R=2,4-dimethoxybenzyl, $Y^1+Y^2$=ethyleneketal and Z=ethyl).

(a) 50 g (0.30 moles) of 2,4-dimethoxybenzaldehyde and 34.4 ml (33.6 g, 0.31 moles) of benzyl amine in 300 ml of dry toluene, in the presence of 1 g of p-toluenesulfonic acid are boiled for 8 hours, while the water formed is continuously eliminated by a water separator. Thereafter toluene is distilled off. The residual oil is dissolved in 120 ml of dioxane and 3.2 g of sodium tetrahydroborate (III) are added with external ice cooling, followed by the addition of a further 3.2 g portion of the same compound after stirring for two hours.

The reaction mixture is allowed to stand for 3 days, diluted with 400 ml of water and the residual oil is shaken with ether, dried over magnesium sulfate, filtered and the filtrate is evaporated into half of its original volume. Thereafter hydrochloric acid in ethanol is added to the ethereal solution, dropwise, under cooling with ice water.

59 g (67%) of benzyl-(2,4-dimethoxybenzyl)amine hydrochloride are obtained, melting at 156° to 157° C. after crystallization from ethyl acetate.

Analysis for $C_{16}H_{20}ClNO_2$ (293,78):

calculated: C: 65.41%, H: 6.86%, Cl: 12.07%, N: 4.77%; found: C: 65.63%, H: 7.30%, Cl: 11.69%, N: 4.72%.

(b) The compound obtained in the step (1a), is converted into the corresponding base and 175 g (0.68 moles) of benzyl (2,4-dimethoxybenzyl)-amine obtained are stirred with 89.6 g (0.38 moles, 64 ml) of diethyl bromomalonate at room temperature until the reaction mixture solidifies. The solidified mixture is triturated with about one liter of ether and the crystalline precipitate is filtered off. (In this way the excess of the starting amine can be recovered as the hydrobromide with a yield of 95%). The filtrate is evaporated and the residual oil is triturated with ethanol. 114.5 g (81%) of diethyl N-benzyl-N-(2,4-dimethoxybenzyl)-amino-malonate are obtained, melting at 62° to 63° C. after crystallization from ethanol.

Analysis for $C_{23}H_{29}NO_6$ (415.47):

Calculated: C: 66.49%, H: 7.04%, N: 3.37%; found: C: 66.58%, H: 7.09%, N: 3.43%.

IR spectrum (KBr): 1750/1725 cm$^{-1}$,d.

(c) 61.7 g (0.149 moles) of diethyl-N-benzyl-N-(2,4-dimethoxybenzyl)-amino-malonate prepared according to Example (1b) are hydrogenated in the presence of about 20 g of a palladium-on-charcoal catalyst, in 500 ml of ethanol, under atmospheric pressure. 47.1 g (97%) of diethyl (2,4-dimethoxybenzylamino)-malonate are obtained, which if desired, can be converted into the corresponding hydrochloride with hydrochloric acid. The HCl salt melts at 122° to 124° C., after crystallization from ethyl acetate.

Analysis for $C_{16}H_{24}ClNO_6$ (361.82):

calculated: C: 53.11%, H: 6.69%, Cl: 9.80%, N: 3.87%; found: C: 52.51%, H: 6.77%, Cl: 10.30%, N: 4.09%.

IR spectrum (film): 3250, 2900, 2850, 1730, 1720 cm$^{-1}$.

$^1$H-NMR spectrum (CDCl$_3$): 1.3 t (6H) 3.78 s (3H); 3.82 s (3H) 4.21 q (4H); 6.20 s (2H); 6.4–6.6 s (2H)+7.3–7.55 m (1H); 7.7 sz s (1H).

(d) 39.6 g (0.122 moles) of diethyl (2,4-dimethoxybenzyl-amino)-malonate prepared according to Example (1c) are boiled with 12.3 g (11.2 ml, 0.146 moles) of diketene in 80 ml of glacial acetic acid for half an hour. The glacial acetic acid is distilled off on water bath, in vacuo, the residual oil is crystallized by trituration with 150 ml of water, whereupon the substance is dissolved in 60 ml of ethyl acetate and recystallized by addition of petroleum ether. 29.6 g (60%) of diethyl-N-(2.4-dimethoxybenzyl)-3-hydroxy-3-methyl-5-oxo-2,2-pyrrolidine-dicarboxylate and/or the tautomer thereof are obtained. Melting point: 106° to 107° C.

Analysis for $C_{20}H_{27}NO_8$ (409.43):

calculated: C: 58.67%, H: 6.65%, N: 3.42%; found: C: 58.79%, H: 6.33%, N: 3.34%.

IR spectrum (KBr): 3400, 2950, 2850, 1730 (1740 v), 1710 cm$^{-1}$.

$^1$H-NMR spectrum (CDCl$_3$): δ1.1 t (3H); 1.17 t (3H); 1.52 s (~3H); 2.08 (<0.1H); 2.65 sz s (2H); 3.75 s (6H); 3.8–4.15 m (4H); 6.7 sz s (2H); 6.25–6.45 m+7.0–7.25 m (3H).

(e) 20.5 g (50 mmoles) of the product of Example (1d) are suspended in 50 ml of dry ether and by two dropping funnels, simultaneously 3.45 g (150 mmoles) of sodium metal in 100 ml of dry ethanol and 12.7 g (50 mmoles) of iodine in 150 ml of dry ether are rapidly added under vigorous stirring, with outer ice cooling. To the mixture 5 g sodium hydrogensulfite dissolved in 200 ml saturated aqueous sodium chloride solution are added. The mixture is poured into a separating funnel and the precipitation of inorganic salts is stopped by adding 60 ml of water. The aqueous phase is separated and shakes with two 100-ml portions of ether. The organic phase is dehydrated with magnesium sulfate, filtered and the filtrate is evaporated. The oily residue (18.5 g) is recrystallized from 30 ml of 2-propanol, 10.9 g (54%) of diethyl 3-acetyl-1-(2,4-dimethoxybenzyl)-4-oxo-2,2-azetidine-dicarboxylate are obtained, melting at 84° to 85° C. after recrystallization from 2-propanol.

Analysis for $C_{20}H_{25}NO_8$ (407.41):
calculated: C: 58.96%, H: 6.19%, N: 3.44%; found: C: 58.99%, H: 6.04%, N: 3.57%.

IR spectrum (KBr): 2900, 1780, 1740, 1710 cm$^{-1}$ $^1$H-NMR spectrum (CDCl$_3$): $\delta$1.12 t (3H); 1.21 t (3H); 2.31 s (3H); 3.75 s (6H); 3.8–4.2 m (4H); 4.53 d (1H) 4.63 d (1H); 4.69 s (1H); 6.3–6.4 m (2H)+7.07 d (1H).

(f$_1$) 25.5 g (0.063 moles) of diethyl-3-acetyl-1-(2,4-dimethoxybenzyl)4-oxo-2,2-azetidine-dicarboxylate prepared according to Example (1e), 6.8 ml (0.126 moles, 7.8 g) of ethylene glycol and 15.8 ml (0.126 moles, 17.9 g) of borotrifluoride diethyl etherate in 100 ml of dry dioxane are allowed to stand at room temperature for 3 days, whereupon 150 ml of water and 150 ml of dichloromethane are added to the reaction mixture. Thereafter the organic phase is separated and shaken with 50 ml of a 5% aqueous sodium hydrogen-carbonate solution and 50 ml of water. The organic phase is separated again, dried with magnesium sulfate, filtered and the filtrate is evaporated. 23.6 g (84% of diethyl-1-(2.4-dimethoxybenzyl)-3-(2-methyl-1,3-dioxolan-2-yl)-4-oxo-2,2-azetidine-dicarboxylate are obtained.

IR spectrum (film): 2900, 1770–1730 cm$^{-1}$ $^1$H-NMR spectrum (CDCl$_3$): $\delta$1.05 5 (3H); 1.31 t (3H); 1.50 s (3H); 3.8 s (6H); 3.85–4.75 m (11H); 6.4 m (2H)+7.1 d (1H).

(f$_2$) 0.5 g (1.2 mmoles) of diethyl-3-acetyl-1-(2,4-dimethoxybenzyl)-4-oxo-2,2-azetidine-dicarboxylate prepared according to Example (1e) are boiled with 0.2 ml of ethyleneglycol in 5 ml of dry toluene, in the presence of p-toluene-sulfonic acid for 25 hours, while water formed in the reaction is continuously eliminated.

The product is then isolated by preparative thin layer chromatography (Kieselgel 60 PF$_{254+366}$, 8:2 mixture of toluene and acetone). 0.11 g (20%) of a compound, which is identical with the product of Example (1f$_1$) are obtained.

EXAMPLE 2

Diethyl-1-(2,4-dimethoxybenzyl)-3-(2-methyl-1,3-oxathiolan-2-yl)-4-oxo-2,2-azetidine dicarboxylate (compound of the formula (IV), in which R=2,4-dimethoxybenzyl, $Y^1+Y^2$=ethylene-hemithioketal and Z=ethyl). 0.5 g (1.2 mmoles) of diethyl 3-acetyl-1-(2,4-dimethoxybenzyl)-4-oxo-2,2-azetidine dicarboxylate in 3 ml of dry tetrahydrofurane are boiled with 0.53 g (3.6 mmoles) of borotrifluoride diethyl etherate and 0.29 g (3.6 mmoles) of mercapto-ethanol for 4 hours, whereupon 10 ml of chloroform are added to the reaction mixturd. The organic phase is separated, shaken with a 5% aqueous sodium hydrogencarbonate solution, the organic phase is separated again, dried with magnesium sulfate, filtered and from the filtrate the product is isolated by preparative thin layer chromatography (Kieselgel 60, PF$_{254+366}$, 8:2 mixture of toluene and acetone). 0.30 g (53%) of the named compound are obtained. The product, which is a mixture of cis and trans isomers is used for the subsequent reactions without any further purification.

EXAMPLE 3

1-(2,4-dimethoxybenzyl)-4-(hydroxymethyl)-3-(2-methyl-1,3-dioxolan-2-yl)-2-azetidinone (compound of the formula (VI), trans isomer, in which $R^1$=2,4-dimethoxybenzyl, $Y^1+Y^2$=ethyleneketal and X=hydroxyl) 13.3 g (35 mmoles) of a cis/trans mixture of ethyl 1-(2,4-dimethoxy-benzyl)-3-(2-methyl-1,3-dioxolan-2-yl)-4-oxo-2-azetidine-carboxylate are dissolved in 30 ml of methanol and 2.66 g (70 mmoles) of sodium tetrahydroburate (III) are added to the solution, under outer cooling with ice water. The reaciton mixture is stirred for about one hour and poured into 100 ml of water. The precipitated oil trans compound is extracted with ethyl acetate, the ethyl acetate extract is dried with magnesium sulfate, filtered and the filtrate is evaporated. The evaporation residue is crystallized from a mixture of diethyl ether and dichloromethane. 2.7 g of a crystalline title compound are obtained. By evaporation of the mother liquor and subjecting the residue to column chromatography (Kieselgel 60, 0.063–0.2 mm, 95:5 mixture of benzena and acetone) further 2.45 g of the product are obtained. Raw yield: 5.15 g (44%) of the named compound, melting at 104° to 105° C.

Analysis for $C_{17}H_{23}NO_6$ (337.36):
calculated: C: 60.52%, H: 6.87%, N: 4.15%; found: C: 60.27%, H: 6.57%, N: 4.22%.

IR spectrum (KBr): 3350, 1725 cm$^{-1}$.

$^1$H-NMR spectrum (CDCl$_3$): $\delta$1.38 s (3H); 1.79 sz s (1H); 3.28 d (2H, J=2.5 Hz); 3.50 m (1H); 3.65 sz s (2H); 3.80 s (3H); 3.82 s (3H); 3.96 m (4H); 4.35 d+4.42 d (2H, $J_{AB}$=15 Hz); 6.5 m (2H)+7.5 d (1H, J=10 Hz).

$^{13}$C-NMR spectrum (CDCl$_3$): $\delta$23.37; 39.43; 55.41; 55.17; 55.58; 59.24; 61.42; 65.07; 65.14; 65.22; 98.71; 104.74; 107.67; 116.58; 131.01; 158.41; 160.87; 166.58.

EXAMPLE 4

1-(2,4-dimethoxybenzyl)-3-(2-methyl-1,3-dioxolan-2-yl)-4-(mesyloxymethyl)-2-azetidinone (compound of the formula (VI), trans isomer, in which $R^1$-2,4-dimethoxybenzyl, $Y^1+Y^2$=ethyleneketal and X=—O—SO$_2$—CH$_3$).

To a solution of 1 g (3 mmoles) of 1-(2,4-dimethoxybenzyl)-4-(hydroxymethyl)-3-(2-methyl-1,3-dioxolan-2-yl)-2-azetidinone obtained in Example 3 in 3 ml of pyridine 0.33 ml (0.5 g, 3.85 mmoles) of mesyl chloride are added dropwise, under outer cooling with ice water. After 15 minutes the mixture is poured onto 15 m of water and shaken with three 6-ml portions of chloroform. The chloroform solution is dried on magnesium sulfate, filtered and the filtrate is evaporated. The residue is crystallized by trituration with ethanol. 0.76 g (62%) of the named compound are obtained, melting at 83° to 84° C. after crystallization from ethanol.

Analysis for $C_{18}H_{25}NO_8S$ (415.45):
calculated: C: 52.04%, H: 6.06%, N: 3.37%; found: C: 52.33%, H: 6.35%, N: 3.06%.

IR spectrum (KBr): 1740 cm$^{-1}$ $^1$H-NMR spectrum (CDCl$_3$): $\delta$1.38 s (3H); 2.93 s (3H); 3.28 d (1H, I=2.5 Hz); 3.62 m (1H); 3.80 s (3H); 3.82 s (3H); 3.95 m (4H); 4.22 d+4.56 d (2H, $J_{AB}$=15 Hz); 4.19–4.34 m (2H); 6.49 m (2H)+7.23 d (1H, I=10 Hz).

$^{13}$C-NMR spectrum (CDCl$_3$): δ23.26; 37.50; 39.45; 52.12; 55.43; 60.05; 65.06; 65.26; 67.54; 98.61; 104.72; 107.33; 116.08; 131.10; 158.58; 161.02; 165.32.

EXAMPLE 5

3-(2-methyl-1,3-dioxolan-2-yl)-4-(mesyloxymethyl)-2-azetidinone (compound of the formula (VI), trans isomer, in which R$^1$=H, Y$^1$+Y$^2$=ethyleneketal and X=—O—SO$_2$—CH$_3$).

2 g (4.8 mmoles) of 1-(2,4-dimethoxybenzyl)-3-(2-methyl-1,3-dioxolan-2-yl)-4-(mesyloxymethyl)-2-azetidinone prepared according to Example 4, 2.6 g (9.6 mmoles) of potassium peroxidisulfate (K$_2$S$_2$O$_8$) and 3.4 g (19.2 mmoles) of disodium hydrogenphosphate. 2H$_2$O are voiled in a mixture of 15 ml of water and 25 ml of acetonitrile for 7 hours. The reaction mixture contains two phases. The phases are separated and the aqueous phase is shaken with three 30-ml portions of ether. The combined organic phases are evaporated, the residue is triturated with 30 ml of water, shaken with three 30-ml portions of chloroform, the chloroform phase is dried with magnesium sulfate, filtered and the filtrate is evaporated. The residual oil is crystallized by trituration with 20 ml of ether. 0.6 g (47%) of 3-(2-methyl-1,3-dioxolan-2-yl-4-(mesyloxymethyl)-2-azetidinone are obtained melting at 110° C.

IR spectrum (KBr): 3200, 2920, 1750 cm$^{-1}$.

$^1$H-NMR spectrum (CDCl$_3$): δ1.44 s (3H); 3.05 s (3H); 3.28 d (1H, I-3 Hz); 3.88 m (1H); 4.01 m (4H); 4.35 m (2H); 6.22 sz s (1H).

$^{13}$C-NMR spectrum (CDCl$_3$): δ23.26; 37.67; 48.98; 61.22; 65.12; 65.36; 70.06; 106.99; 165.94.

EXAMPLE 6

1-(2,4-dimethoxybenzyl)-3-(2-methyl-1,3-dioxolan-2-yl)-4-(iodomethyl)-2-azetidinone (compound of the formula (VI), trans isomer, in which R$^1$=2,4-dimethoxybenzyl, Y$^1$+Y$^2$=ethyleneketal, X=iodine).

5 g (12 mmoles) of trans 1-(2,4-dimethoxybenzyl)-3-(2-methyl-1,3-dioxolan-2-yl)-4-(mesyloxymethyl)-2-azetidinone prepared according to Example 4 are boiled with 7.5 g. (50 mmoles) of sodium iodide for 4 hours with stirring. The mixture is evaporated to dryness, triturated with water and the crystalline substance obtained is recrystallized from ethanol. 4.5 g of the named compound are obtained, melting at 79° to 80° C.

IR spectrum (KBr): 2920, 1745 cm$^{-1}$ $^1$H-NMR (acetone-d$_6$): δ1.34 s (3H); 3.11 d (1H, I=2 Hz); 3.3–3.75 m (3H); 3.79 s (3H); 3.84 s (3H); 3.92 m (4H); 4.13 d+4.46 d (2H, I$_{AB}$=16 Hz); 6.50 m (2H)+7.25 d (1H, I=10 Hz).

$^{13}$C-NMR (CDCl$_3$): δ6.53; 23.71; 38.97; 53.56; 55.37; 64.18; 65.06; 65.17; 98.45; 104,46; 107.33; 115.91; 130.89; 158.43; 160.84; 165.05

EXAMPLE 7

4-(cyanomethyl)-1-(2,4-dimethoxybenzyl)-3-(2-methyl-1,3-dioxolane-2-yl)-2-azetidinone (compound of the formula (VI), trans isomer, in which R$^1$=2,4-dimethoxybenzyl, Y$^1$+Y$^2$=ethyleneketal and X=cyano).

1 g (2.2 mmoles) of trans-1-(2,4-dimethoxybenzyl)-3-(2-methyl-1,3-dioxolan-2-yl)-4-(iodomethyl)-2-azetidinone prepared according to Example 6 and 0.25 g (5.1 mmoles) of sodium cyanide are stirred in 5 ml of dry dimethyl formamide at room temperature, for 24 hours. The reaction mixture is poured into 15 ml of a saturated aqueous sodium chloride solution. The mixture is shaken with three 20-ml portions of ether, the ethereal phase is dried with magnesium sulfate, filtered and the filtrate is evaporated. The oily residue is purified by preparative thin layer chromatography (Kieselgel 60 PF$_{254+366}$, a 8:2 mixture of benzene and acetone). 0.46 g (59%) of the named compound are obtained.

IR spectrum (film): 2920, 1755 cm$^{-1}$ $^1$H-NMR spectrum (CDCl$_3$): δ1.38 s (3H); 2.56+2.54 ABX (2H, I$_{gem}$=17 Hz, I$_{vic}$=4.7 5.8 Hz); 3.24 d (1H; J=2.3 Hz); 3.55 ddd (1H, I=5.8, 4.7, 2.3 Hz); 3.80 s (3H); 3.82 s (3H); 3.95 m (4H); 4.21 d+4.50 d (2H; J$_{AB}$=15 Hz); 6.40–6.55 m (2H) +7.21 d (1H, I=10 Hz).

EXAMPLE 8

3-(2-methyl-1,3-dioxolan-2-yl)-4-(iodomethyl)-2-azetidinone (compound of the formula (VI), trans isomer, in which R$^1$=H, Y$^1$+Y$^2$=ethyleneketal and X=iodine).

1 g (3.8 mmoles) of 3-(2-methyl-1,3-dioxolan-2-yl)-4-(mesyloxymethyl)-2-azetidinone in 10 ml of dry acetone are boiled with 2 g (13.3 mmoles) of sodium iodide for 4 hours. The mixture is evaporated to dryness, the evaporation residue is triturated with 30 ml of water, shaken with three 30-ml portions of chloroform, and the chloroform phase is dried with magnesium sulfate, filtered and the filtrate is evaporated. The oily product is purified by preparative thin layer chromatography (Kieselgel 60 PF$_{254+366}$, a 7:8 mixture of benzene and acetone). The product melts at 85° to 86° C. after crystallization from a mixture of ethyl acetate and petroleum ether.

Analysis for C$_8$H$_{12}$INO$_3$ (297.10):

calculated: I: 42.72%, N: 4.71%; found: I: 42.45%, N: 5.00%.

EXAMPLE 9

The separation of cis and trans ethyl 1-(2,4-dimethoxybenzyl)-3-(2-methyl-1,3-dioxolan-2-yl)4-oxo-2-azetidine-carbylate (compounds of the formula (V)).

By subjecting 11.7 g of the cis/trans isomer mixture to column chromatography (Kieselgel 60, 0.063–0.200 mm, eluting agent: benzene and then a mixture of benzene and acetone, increasing the proportion of acetone gradually up to a ratio of 1:9). 6.39 g of an oily trans isomer, 3 g of a mixture of cis and trans isomers and 0.85 g of cis isomer are obtained.

Cis isomer $^1$H-NMR spectrum (CDCl$_3$): 1.31 t (3H); 1.42 s (3H); 3.64 d (1H, I=6 Hz); 3,76 s (3H); 3,79 s (3H); 3.85–4.10 m (5H); 4.20 q (2H); 4.20+4.70 ABq (2H); 6.42 m (2H); 7.12 d (1H, I=10 Hz).

trans isomer $^1$H-NMR spectrum (CDCl$_3$): 1.23 t (3H); 1.38 s (3H); 3.40 d (1H, I=2.5 Hz); 3.76 s (3H); 3.79 s (3H); 3.90–4.06 m (5H); 4.17 q (2H); 4.20+4.64 ABq (2H); 6.46 m (2H); 7.15 d (1H, I=10 Hz).

EXAMPLE 10

The reaction steps disclosed in Examples (1a) and (1b) can be carried out also without the isolation of the product of Example (1a) in the following manner:

109.7 g (0.66 moles) of 2,4-dimethoxy-benzyldehyde and 72 ml (0.66 moles) of benzylamine in 660 ml of methanol are stirred at room temperature for 20 minutes (suspension and later a clear solution is obtained), followed by a portionwise addition of 13.2 g (0.33 moles) of sodium tetrahydroburate (III).

The progress of the reaction is monitored by thin layer chromatography (Kieselgel G, according to Stahl, a 9:1 mixture of benzene and acetone). When the reaction is complete, the mixture is evaporated to dryness in vacuo, to the residue 300 ml of water are added and it is extracted with 500 ml of ether. The aqueous phase is extracted with two 200-ml portions of ether. The combined ethereal phases are dried with magnesium sulfate, filtered and to the ethereal solution 112 ml (0.66 moles) of diethyl bromomalonate and 93 ml (0.66 moles) of triethyl amine are added. The reaction mixture is stirred at room temperature for 2 to 3 days. The precipitated triethyl ammoniumbromide is filtered off and washed with ether. The mother liquor is evaporated and the residue is crystallized from 150 ml of ethanol. 210 g of a crude product are obtained, which is recrystallized from 400 ml of ethanol to give 197 g (72%) of diethyl N-benzyl-N-(2,4-dimethoxy-benzyl)-amino-malonate. The physical constants of the product are identical with the data given in Example (1b).

CHART A

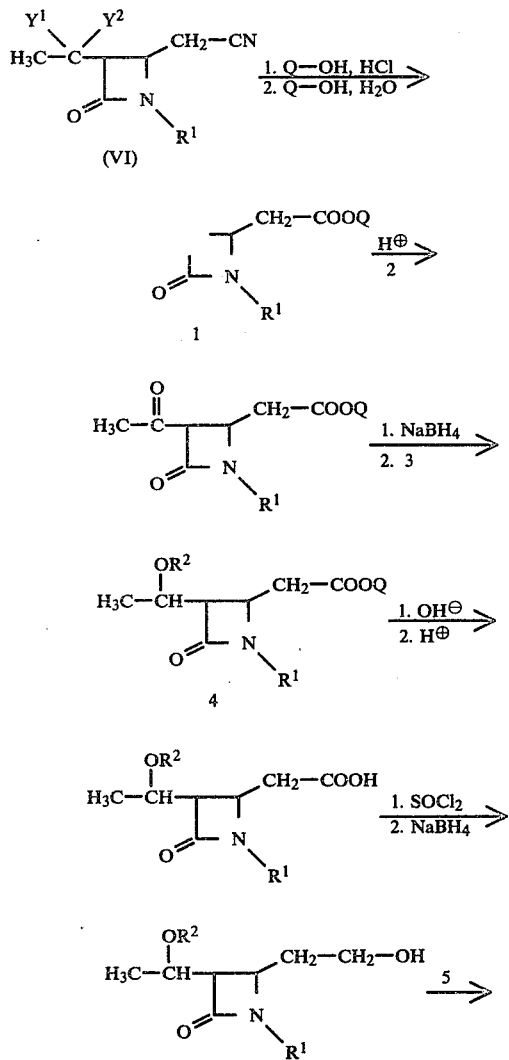

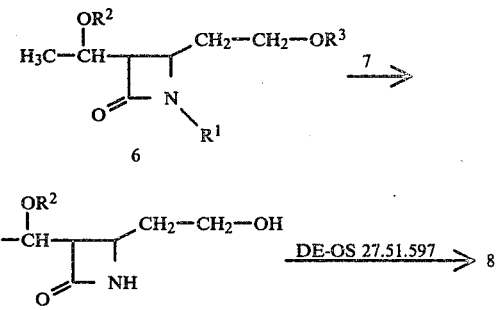

-continued
CHART A

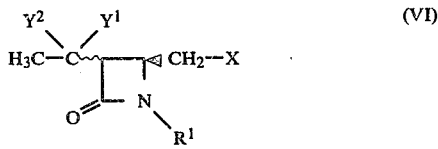

TEXT OF CHART A
1 Q = alkyl, preferably methyl or ethyl
2 acetone
3 2.chloroformic acid p-nitro-benzylester
4 $R^2$ = p-nitro-benzyloxycarbonyl
5 2,3-dihydropyrane or acetic anhydride
6 $R^3$ is tetrahydropyranyl or acetyl
7 elimination of $R^1$ and $R^3$
8 thienamycin

We claim:
1. A compound of the formula (VI)

(VI)

wherein
$R^1$ is hydrogen, benzyl or benzyl substituted by one or two methoxy groups;
X is hydroxyl, halogen, cyano, or an —O—$SO_2$—$R^2$ group, in which
$R^2$ is lower alkyl or aryl; and
$Y^1$ and $Y^2$ together with the carbon atom to which they are attached form together a 1,3-dioxolan-2-yl group or a thio analog thereof.

2. The compound defined in claim 1 wherein $R^1$ is 2,4-dimethoxy-benzyl, X is —$OSO_2R^2$, and $R^2$ is methyl or tolyl.

3. The compound defined in claim 1 which is 1-(2,4-dimethoxy-benzyl)-4-(hydroxymethyl)-3-(2-methyl-1,3-dioxolan-2-yl)-2-azetidinone.

4. The compound defined in claim 1 which is 1-(2,4-dimethoxy-benzyl)-4-(mesyloxymethyl)-3-(2-methyl-1,3-dioxolan-2-yl)-2-azetidinone.

5. The compound defined in claim 1 which is 1-(2,4-dimethoxy-benzyl)-4-(iodomethyl)-3-(2-methyl-1,3-dioxolan-2-yl)-2-azetidinone.

6. The compound defined in claim 1 which is 1-(2,4-dimethoxy-benzyl)-4-(cyanomethyl)-3-(2-methyl-1,3-dioxolan-2-yl)-2-azetidinone.

7. The compound defined in claim 1 which is 3-(2-methyl-1,3-dioxolan-2-yl)-4-(mesyloxymethyl)-2-azetidinone.

8. The compound defined in claim 1 which is 3-(2-methyl-1,3-dioxolan-2-yl)-4-(iodomethyl)-2-azetidinone.